(12) United States Patent
Dyck et al.

(10) Patent No.: US 6,984,754 B1
(45) Date of Patent: Jan. 10, 2006

(54) ALIPHATIC AMINO CARBOXYLIC AND AMINO PHOSPHONIC ACIDS AMINO NITRILES AND AMINO TETRAZOLES AS CELLULAR RESCUE AGENTS

(75) Inventors: Lillian E. Dyck, Saskatoon (CA); Bruce A. Davis, Saskatoon (CA); Ya-Dong Liu, Freemont, CA (US); David A. Durden, Calgary (CA); Alan A. Boulton, Saskatoon (CA); I. Alick Paterson, deceased, late of Saskatoon (CA); by Brenda Kennedy, legal representative, Saskatoon (CA); by Kevin Rogers, legal representative, Saskatoon (CA)

(73) Assignee: University of Saskatchewan Technologies Inc., Saskatoon (CA)

( * ) Notice: Subject to any disclaimer, the term of this patent is extended or adjusted under 35 U.S.C. 154(b) by 0 days.

(21) Appl. No.: 09/646,110

(22) PCT Filed: Mar. 25, 1999

(86) PCT No.: PCT/CA99/00250
§ 371 (c)(1),
(2), (4) Date: Nov. 5, 2001

(87) PCT Pub. No.: WO99/48858
PCT Pub. Date: Sep. 30, 1999

Related U.S. Application Data

(60) Provisional application No. 60/079,488, filed on Mar. 26, 1998, and provisional application No. 60/079,489, filed on Mar. 26, 1998.

(51) Int. Cl.
C07C 205/00 (2006.01)

(52) U.S. Cl. .................................. 562/553; 514/114
(58) Field of Classification Search ................ 562/553; 514/114
See application file for complete search history.

(56) References Cited

U.S. PATENT DOCUMENTS

| | | | |
|---|---|---|---|
| 3,991,208 A | * | 11/1976 | Dudzinski et al. ........... 514/554 |
| 4,548,726 A | * | 10/1985 | Morris-Sherwood et al. . 252/75 |
| 4,804,500 A | * | 2/1989 | Miller et al. |
| 4,961,873 A | * | 10/1990 | Ho et al. |
| 5,565,290 A | * | 10/1996 | Itakura et al. |
| 5,723,239 A | * | 3/1998 | Itakura et al. |

FOREIGN PATENT DOCUMENTS

| | | |
|---|---|---|
| DE | 11 39 738 | 11/1962 |
| DE | 15 67 221 | 4/1970 |
| DE | 20 52 256 | 5/1971 |
| DE | 24 42 239 | 3/1975 |
| DE | 25 55 769 | 6/1977 |
| FR | 2 451 913 | 10/1980 |
| WO | WO 92/15551 | 9/1992 |
| WO | WO 96/05286 | 2/1996 |
| WO | WO 97/45115 | 12/1997 |

OTHER PUBLICATIONS

Tien et al, JACS, 1955, vol. 77 pp. 6696–6698.*
CA 1998:45464: Hamper et al, Journal of Organic Chemistry, vol. 63 (3) (1998) pp. 708–718.*
CA 1996:637648.*
CA 1995:878827, WO 9512610.*
CA 1993:46312, Nakamura et al, Colloids and Surfaces (1992) vol. 67, pp. 183–193.*
CA 1992:59021, Bulletin of the Korean Chemical Society, 1991, vol. 12(5) p. 589.*
CA 1991:27105 CA 1989:38631, ES patent 2003836.*
CA 1987:440328.*
Nishimura, Kuniko et al. "Inactivation of Monoamine Oxidase B by Analogues of the Anticonvulsant Agent Milacemide (2–(n–Pentylamino) acetamide)", Journal of Medicinal Chemistry, vol. 36, No. 4, pp. 446–448, 1993.
Satzinger, Gerhard. "5–Substituted and 1,5–condensed tetrazoles", Chemical Abstracts, vol. 55, No. 15, p. 14441, 1961.
Leonard, Frederick et al. "Potential Antiviral Agents", Journal of the American Chemical Society, vol. 78, No. 6, pp. 1199–1201, 1956.
Boit, Hans–G. Beilsteins Handbuch Der Organischen Chemie, 4th Ed., 3rd Suppl.,vol. 4, Part 2, p. 1137, 1963.
Luckenbach, Reiner. "Beilsteins Handbuch Der Organischen Chemie". 4th Ed., 4th Suppl., vol. 4, Part 3, p. 2386, 1980.
Miyagishi, Shigeyoshi et al. "Phase Transition of N–Acyl Amino Acids with Different Acyl Group", Bulletin of the Chemical Society of Japan, vol. 59, No. 2, pp. 557–562, 1986.

(Continued)

Primary Examiner—Rita Desai
Assistant Examiner—Hector M. Reyes
(74) Attorney, Agent, or Firm—Bereskin & Parr; Patricia Power

(57) ABSTRACT

Novel compounds of formula (I) are described wherein: $R_1=(CH_2)_m CH_3$ where m is 0 or an integer in the range from 1 to 16, or an alkenyl, alkynyl, alkoxy, alkylthio, or alkyl sulfinyl group having from 2 to 17 carbon atoms; $R_2$=H, $CH_3$ or $CH_2CH_3$; $R_3$=H or $CH_3$; $R_4$H or $CH_3$; $R_5$=lower alkyl having from 1 to 5 carbon atoms; n is an integer in the range from 1 to 3, and X is carboxyl (COOH) or carbalkoxy ($COOR_5$), cyano (C≡N), phosphonic acid ($PO_3H_2$), phosphonate ester ($PO_3[R_5]_2$) or 5-tetrazole, and pharmaceutically acceptable salts thereof. Preferably, the compounds are optically pure enantiomers of the R— or S—configuration in which $R_3=R_4=R_5$=H, $R_2$=$CH_3$ and $R_1$ is a saturated aliphatic chain of one to five carbon atoms. The compounds are useful as cellular rescue agents (I)

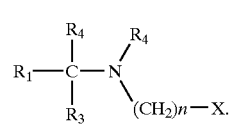

20 Claims, No Drawings

OTHER PUBLICATIONS

Kirino, Osamu et al."Studies on anti–fusarium disease activity of aminonitrile derivatives . . . ", *Chemical Abstracts,* vol. 92, No. 23, p. 167, 1980.

Corse, Joseph et al. "N–Substituted 2–Methoxy–6–chloro–9–aminoacridines Derived from Unsymmetrical Aliphatic Amines", Journal of the American Chemical Society, vol. 68, pp. 1905–1910, 1946.

Ishizuka, Tetsuo et al. "Alkyl–beta–amines from long–chain olefins", Chemical Abstracts, vol. 74, No. 8, p. 70, 1971.

Sakakibara, Seizaburo et al. "Cationic surface–active agents from long–chain alkyl amines and acrylonitrile", Chemical Abstracts, vol. 55, No. 8, p. 7275, 1961.

Takahashi, Hisashi, "Effects of derivatives of gamma–amniobutyric acid . . . ", Chemical Abstracts, vol. 55, No. 23, p. 23837, 1961.

* cited by examiner

ALIPHATIC AMINO CARBOXYLIC AND AMINO PHOSPHONIC ACIDS AMINO NITRILES AND AMINO TETRAZOLES AS CELLULAR RESCUE AGENTS

FIELD OF THE INVENTION

The invention relates to novel aliphatic amino carboxylic and amino phosphoric acids, amino nitrites and amino tetrazoles, their salts, compositions containing such compounds and to the use of such compounds as cellular rescue agents in human and veterinary medicine.

BACKGROUND OF THE INVENTION

Neurodegenerative disorders (for example, chronic disorders such as Alzheimer's disease, Parkinson'disease, Huntington's disease, Picks's disease, amyotrophic lateral sclerosis and glaucoma as well as acute injuries like stroke, head trauma, Bell's palsy and spinal cord injuries) are now believed to involve apoptotic processes.

Deprenyl, the aliphatic propargylamines, their respective desmethyl analogues and rasagiline have been shown to protect and rescue damaged neurons in several models of degeneration [1–16]. The propargyl group was thought to be a requirement for the protective or rescuing activity of these drugs. Previous studies have examined the N-demethylation and/or depropargylation of these drugs [7, 171].

It has been known for some time that some aliphatic and aromatic acetylenic compounds react with P450 enzymes. One of these reactions results in oxidation of the terminal carbon of the acetylenic functional group to form the corresponding acid [18–20]. The possibility of oxidation of the N-acetylene group of the aliphatic propargylamines to form carboxylic acid metabolites has not been previously addressed. The potential of related acidic compounds (the amino phosphonic acids and amino tetrazoles) and precursors to such compounds (amino nitrites and amino esters) as antiapoptotic agents had also not been previously considered.

The present inventors have found that aliphatic amino carboxylic and amino phosphonic acids, amino nitriles and amino tetrazoles are antiapoptotic agents and may be useful as cellular rescue agents in human and animal treatments.

SUMMARY OF THE INVENTION

The present invention relates to a compound of the general formula (I),

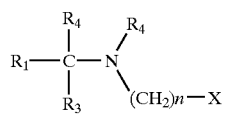

Formula (I)

wherein:
$R_1$ is $(CH_2)_m CH_3$ where m is 0 or an integer in the range from 1 to 16, or an alkenyl, alkynyl, alkoxy, alkylthio, or alkyl sulfinyl group having from 2 to 17 carbon atoms. $R_1$ may be unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N,
$R_2$=H, $CH_3$ or $CH_2CH_3$,
$R_3$=H or $CH_3$,
$R_4$=H or $CH_3$,
$R_5$=lower alkyl having from 1 to 5 carbon atoms,
n is an integer in the range from 1 to 3,
and X is carboxyl (COOH), carbalkoxy ($COOR_5$), cyano (C≡N), phosphonic acid ($PO_3H_2$), phosphonate ester ($PO_3[R_5]_2$) or 5-tetrazole, and the salts thereof, particularly pharmaceutically acceptable salts thereof.

Compounds of the general formula I in which $R_1$, $R_2$ and $R_3$ differ from one another are chiral. It has been found that the R-enantiomers of some of these classes or sub-classes of compounds (and the S-enantiomers for other classes or subclasses) are useful as cellular rescue agents for the treatment and prevention of diseases in which cell death occurs by apoptosis, such as in many neurodegenerative disorders. For a particular class or subclass of compounds the inactive enantiomer does not prevent apoptosis but can antagonize the antiapoptotic actions of the active enantiomers, and are useful as research tools. The achiral compounds also display cellular rescue properties.

The present invention also relates to the use of compounds of general formula I, as defined above, and salts thereof, as cellular rescue agents for the treatment and prevention of diseases in which cell death occurs by apoptosis including but not limited to, stroke, head trauma, Bell's palsy, spinal cord and other nerve crush injuries, Alzheimer's disease, Parkinson's disease, Pick's disease, amyotrophic lateral sclerosis, Huntington's disease, multiple sclerosis, cardiac myopathies, nephropathy, retinopathy, diabetic complications, glaucoma, as well as idiopathic neuropathies. Accordingly, the present invention provides a method for treating a condition wherein cell death occurs by apoptosis comprising administering an effective amount of a compound of the formula I to an animal in need thereof.

DETAILED DESCRIPTION OF PREFERRED EMBODIMENTS

Compounds of the Invention

The present invention relates to compounds of the general formula I,

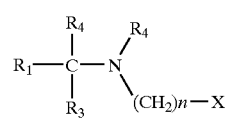

Formula (I)

wherein:
$R_1$ is $(CH_2)_m CH_3$ where m is 0 or an integer in the range from 1 to 16, or an alkenyl, alkynyl, alkoxy, alkylthio, or alkyl sulfinyl group having from 2 to 17 carbon atoms. $R_1$ may be unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N,
$R_2$=H, $CH_3$ or $CH_2CH_3$,
$R_3$=H or $CH_3$,
$R_4$=H or $CH_3$,
$R_5$=lower alkyl having from 1 to 5 carbon atoms,
n is an integer in the range from 1 to 3,
and X is carboxyl (COOH), carbalkoxy ($COOR_5$), cyano (C≡N), phosphonic acid ($PO_3H_2$), phosphonate ester ($PO_3[R_5]_2$) or 5-tetrazole, and the salts thereof.

In a preferred embodiment, the present invention provides a compound of the Formula I (as described above) wherein $R_1=(CH_2)_mCH_3$ where m is 0 or an integer in the range from 1 to 16,
$R_2=CH_3$,
$R_3=H$,
$R_4=H$ or $CH_3$,
$R_5$=lower alkyl having from 1 to 5 carbon atoms,
n is an integer in the range from 1 to 3,
and X is carboxyl (COOH) or carbalkoxy ($COOR_5$), cyano (C≡N), phosphonic acid ($PO_3H_2$), phosphonate ester ($PO_3[R_5]_2$) or 5-tetrazole, or a pharmaceutically acceptable salt thereof.

Preferred compounds of the invention include:
2-(2-Propylamino)acetic acid;
2-(1-Hexylamino)acetic acid;
(S)-2-(2-Heptylamino)acetic acid;
3-(2-Propylamino)propionic acid;
3-(1-Hexylamino)propionic acid;
(R)-3-(2-Heptylamino)propionic acid;
2-(2-Propylmethylamino)acetic acid;
2-(1-Hexylmethylamino)acetic acid;
(S)-2-(2-Heptylmethylamino)acetic acid;
3-(2-Propylmethylamino)propionic acid;
3-(1-Hexylmethylamino)propionic acid;
(R)-3-(2-Heptylmethylamino)propionic acid;
2-(2-Propylamino)acetonitrile;
(R)-2-(2-Pentylamino)acetonitrile;
2-(1-Hexylamino)acetonitrile;
(S)-2-(2-Heptylamino)acetonitrile;
(R)-3-(2-Heptylamino)propionitrile;
2-(2-Propylmethylamino)acetonitrile;
(R)-2-(2-Pentylmethylamino)acetonitrile;
2-(1-Hexylmethylamino)acetonitrile;
(S)-2-(2-Heptylmethylamino)acetonitrile;
(R)-3-(2-Heptylmethylamino)propionitrile;
2-(2-Propylamino)ethanephosphonic acid;
(R)-2-(2-Pentylamino)ethanephosphonic acid;
(S)-2-(2-Heptylamino)ethanephosphonic acid;
2-(2-Propylmethylamino)ethanephosphonic acid;
(S)-2-(2-Heptylmethylamino)ethanephosphonic acid; and
(R)-2-(2-Heptylamino)ethane-5-tetrazole.

Compounds of formula I which are optically pure enantiomers are novel. Achiral and racemic compounds are novel with the exception of the following exclusions, although their properties as cellular rescue agents are not known.

a) for X=COOH; n=1; $R_3=R_4=H$, exclude compounds for which:
$R_2=H$ and m=1 to 4, 6, 7, 9, 11, or 13, and
$R_2=CH_3$ and m=0, 1 or 2.

b) for X=COOH; n=1; $R_3=H$; $R_4=CH_3$, exclude compounds for which:
$R_2=H$ and m=2 or 3, and
$R_2=CH_3$ and m=0.

c) for $X=COOR_5$; n=1; $R_3=R_4=H$, exclude compounds for which:
$R_2=H$ and m=1 to 4, or 9, and
$R_2=CH_3$ and m=0 or 1, and
$R_5$=methyl, ethyl, t-butyl.

d) for X=COOH; n=2; $R_3=R_4=H$, exclude compounds for which:
$R_2=H$ and m=1 to 4, 6, 9 or 11, and
$R_2=CH_3$ and m=0, 1 or 4.

e) for X=COOH; n=2; $R_3=H$; $R_4=CH_3$, exclude compounds for which:
$R_2=H$ and m=1 or 2.

f) for $X=COOR_5$; n=2; $R_3=R_4=H$, exclude compounds for which:
$R_2=H$ and m=1 to 5, 9 or 15,
$R_2=CH_3$ and m=0 or 1, and
$R_5$=methyl, ethyl, t-butyl.

g) for $X=COOR_5$; n=2; $R_3=H$; $R_4=CH_3$, exclude compounds for which:
$R_2=H$ and m=1 or 2,
$R_2=CH_3$ and m=0, and
$R_5$=methyl, ethyl, t-butyl.

h) for X=COOH; n=3; $R_3=R_4=H$, exclude compounds for which:
$R_2=H$ and m=2 or 6.

i) for $X=COOR_5$; n=3; $R_3=R_4=H$, exclude compounds for which:
$R_2=H$ and m=2,
$R_2=CH_3$ and m=0 or 1, and
$R_5$=methyl, ethyl, t-butyl.

j) for X=C≡N (cyano); n=1; $R_3=R_4=H$, exclude compounds for which:
$R_2=H$ and m=1, 2, 4, 5 or 6, and
$R_2=CH_3$ and m=0, 1 or 2.

k) for X=C≡N; n=1; $R_3=H$; $R_4=CH_3$, exclude compounds for which:
$R_2=H$ and m=1, and
$R_2=CH_3$ and m=0.

l) for X=C≡N; n=2; $R_3=R_4=H$, exclude compounds for which:
$R_2=H$ and m=1, 2, 3, 4 or 6, and
$R_2=CH_3$ and m=0, 1 or 4.

m) for X=C≡N; n=2; $R_3=H$; $R_4=CH_3$, exclude compounds for which:
$R_2=H$ and m=2, and
$R_2=CH_3$ and m=0.

n) for X=C≡N; n=3; $R_3=R_4=H$, exclude compounds for which:
$R_2=H$ and m=1 to 4, and
$R_2=CH_3$ and m=1 or 2.

o) for $X=PO_3H_2$; n=2; $R_3=R_4=H$, exclude compounds for which:
$R_2=CH_3$ and m=0, 1 or 5.

p) for $X=PO_3(R_5)_2$; n=2; $R_3=R_4=H$, exclude compounds for which:
$R_2=CH_3$ and m=0 or 1, and
$R_5$=ethyl.

q) for X=5-tetrazole; n=2, $R_3=R_4=H$, exclude compounds for which:
$R_2=CH_3$ and m=0.

Particularly preferred are those of the R and S configurations, depending on the subclass of compound. Methods of resolving the racemates are known. Suitable methods include fractional crystallization, derivatization of the racemate followed by stereospecific enzymatic removal of the attached group, and chromatography. It is preferred, however, to make chiral compounds of formula I from chiral reactants, using reactions that do not destroy the stereochemistry. When referring to enantiomers, it is preferred that an enantiomer shall not contain more than 3% of the compound of the opposite configuration. It is particularly preferred that an enantiomer contain less than 1% of the corresponding enantiomer of the opposite configuration.

Some of the inactive enantiomers for a given class or subclass of compounds strongly antagonize the antiapoptotic actions of the active enantiomers, and are useful as research tools.

The invention extends to salts of compounds of formula I. For administration the salts should be pharmaceutically acceptable, but other salts may be useful, for example, in synthesis or for purification.

Methods of Preparing Compounds of the Invention

Compounds of the invention can be prepared in a variety of different ways. One process involves the addition of a primary amine of formula (II)

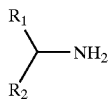
(II)

across the olefinic double bond of α,β-unsaturated carboxylic acid esters (such as methyl acrylate), of vinylphosphonic acids esters or of α,β-unsaturated nitriles (such as acrylonitrile) of formula (III)[21], $$H_2=CH-X \qquad (III)$$

wherein X is a polarized group such as carboxylic ester, phosphonic ester or nitrile to give the corresponding N-alkylamino propionic esters, ethanephosphonic esters and propionitriles.

It is possible to use an amine of the formula (II) in which $R_1$ differs from $R_2$ in the form of a racemate and to separate the enantiomers subsequently, but it is preferred to use an amine in substantially enantiomerically pure form.

Chiral primary amines (R- or S-forms) were prepared by recrystallization of the tartrates of the racemates from methanol [22], except for (R) and (S)-2-butylamines which were purchased from Aldrich Chemical Co. Enantiomeric purity was determined using gas chromatography with a chiral capillary column and chiral derivatizing agent [23]. In analogy to the above, chiral primary amines can also be added to the C—C double bond of methyl acrylate, diethyl vinylphosphonate or acrylonitrile to give the corresponding chiral methyl N-alkylaminopropionate, chiral diethyl N-alkylaminoethanephosphonate or chiral N-alkylaminopropionitrile.

In one embodiment, an excess of a chiral amine adds to the olefinic bond of acrylonitrile, as depicted in the following scheme.

Excess Amine and Acrylonitrile

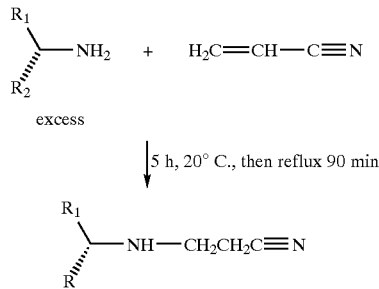

where $R_1$=hydrogen, methyl or ethyl and
$R_2$=methyl, ethyl, propyl, butyl, pentyl, hexyl.

In another embodiment an excess of the amine can be added to the olefinic double bond of diethyl vinylphosphonate to give the corresponding diethyl N-alkylaminoethanephosphonate. Hydrochloric acid hydrolysis of the aminophosphonic diester yields the corresponding aminophosphonic acid as the hydrochloride salt.

In yet another embodiment an excess of the amine can be added to the olefinic double bond of methyl acrylate to give the corresponding methyl N-alkylaminopropionate [24]. Hydrolysis of the carboxylate ester with hydrochloric acid produces an amino acid as its hydrochloride salt, in accordance with the following reaction scheme:

Hydrolysis of Esters

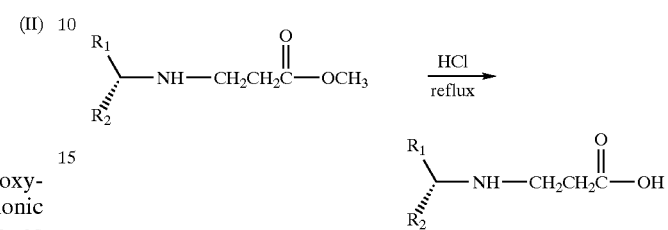

A second process to give compounds of the invention which contain only one carbon atom between the nitrogen atom and the functional group involves condensing a primary aliphatic amine of formula (II) with a bromomethyl reactant of formula (IV)

$$LCH_2X \qquad (IV)$$

wherein L is a leaving group, for example a halide, tosyl or mesyl group (bromide is preferred), and X is carboalkoxy (carbomethoxy or carbethoxy is preferred), nitrile or phosphodiethoxy. Again, the amine can be used in racemic or enantiomerically pure form. In one preferred embodiment, two equivalents of the amine are reacted with one equivalent of the bromomethyl analogue of formula (IV) to form the required aminomethanecarboxylate (glycine) ester and the hydrobromide salt of the amine, which can be isolated and reused, in accordance with the following reaction scheme.

Two Equivalents of Amine and One Equivalent of Bromomethyl Ester in Ether

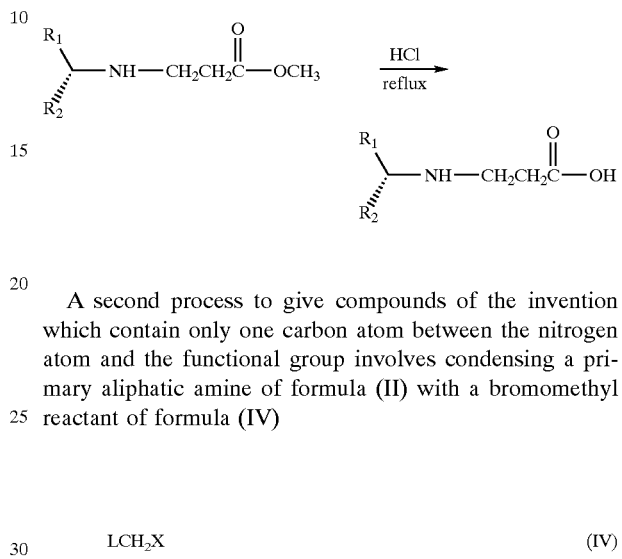

In another preferred embodiment, two equivalents of the amine are reacted with one equivalent of the bromomethyl analogue of formula (IV) to form the required aminomethane nitrile (aminoacetonitrile) and the hydrobromide salt of the amine, which can also be isolated and reused, in accordance with the following reaction scheme.

Two Equivalents of Amine and One Equivalent of Bromoacetonitrile in Ether

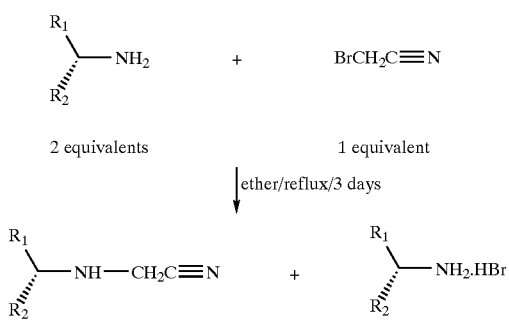

2 equivalents                    1 equivalent

Another route to compounds of the invention involves trifluoroacetylation of the amine, followed by reaction with bromomethyl, bromoethyl or bromopropyl analogues of esters of carboxylic acids or nitriles of formula (V).

$$L(CH_2)nX \quad\quad (V)$$

wherein L is a leaving group, for example a halide, tosyl or mesyl group (bromide is preferred), n is 1, 2 or 3 and X is carboalkoxy (methoxy or ethoxy is preferred), nitrile or phosphodiethoxy.

The amine can be used in racemic or enantiomerically pure form. The amine is reacted with trifluoroacetic anhydride or a trifluoroacetyl halide in an inert organic solvent, for instance a chlorinated hydrocarbon such as methylene dichloride, chloroform or carbon tetrachloride, and a base, for example an organic base such as triethylamine. The N-trifluoroacetylamine is then refluxed with a bromo compound of formula (V), suitably in the presence of a base such as potassium t-butoxide in a polar solvent, for example acetonitrile, and in the presence of a crown ether catalyst, for example 18-crown-6. The product of this reaction is then hydrolyzed, suitably by reaction with a base such as an alkali metal hydroxide in an alcoholic solution.

Tetrazole compounds of the invention were prepared by the addition of azide ion to a nitrile triple bond [25]. Again, the amine can be used in racemic or enantiomerically pure form. In one preferred embodiment azide ion is generated by the slow addition of aluminum chloride to a solution/suspension of sodium azide in tetrahydrofuran at 0° C. To the resulting solution of aluminum azide is added the nitrile (prepared as in the pathways described above) in tetrahydrofuran at room temperature, followed by stirring for 2 hours and then gentle refluxing for several hours, according to the following scheme.

Addition of Azide Ion to Nitrile

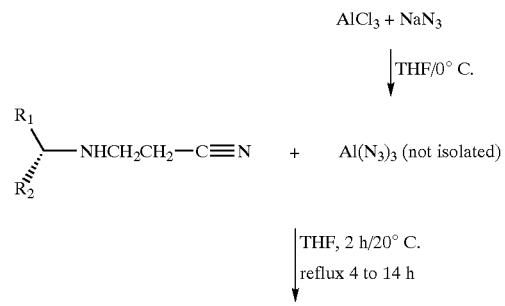

-continued

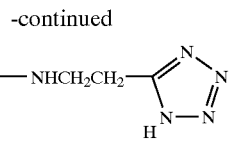

N-Methylation of the various secondary amines described above is achieved by reductive methylation using formaldehyde and sodium phosphite [26]. Again, the amine can be used in racemic or enantiomerically pure form. An amino carboxylate ester or amino nitrile (as the hydrochloride salt or free base) is dissolved in aqueous sodium dihydrogen phosphite and reacted with an excess of 37% aqueous formaldehyde at 60° C. for 15 min. The product is isolated by ether extraction after basification of the ice-cold reaction mixture with sodium hydroxide. A preferred embodiment is shown in the following reaction scheme.

N-Methylation of an Amino Ester

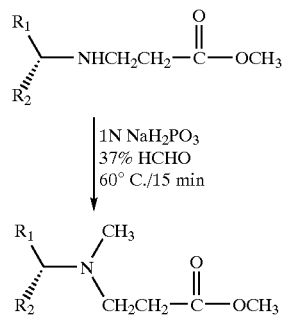

Yet another preferred embodiment is shown in the following reaction scheme.

N-Methylation of an Amino Nitrile

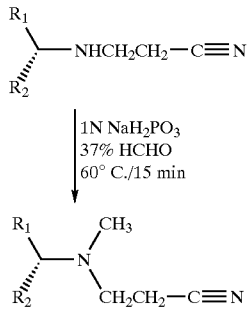

Therapeutic Methods of the Invention

As hereinbefore mentioned, the compounds of the formula I (as described above) have many therapeutic applications.

In one aspect, the present invention provides a method for treating or preventing a condition wherein cell death occurs by apoptosis comprising administering an effective amount of a compound of the formula I to an animal in need thereof.

The term "effective amount" as used herein means an amount effective, at dosages and for periods of time necessary to achieve the desired result. The term "animal" as used herein includes all members of the animal kingdom including humans.

In another aspect, the present invention provides a use of a compound of the formula I to treat or prevent a condition wherein cell death occurs by apoptosis.

In yet a further aspect, the present invention provides a use of a compound of the formula I to prepare a medicament to treat or prevent a condition wherein cell death occurs by apoptosis.

Conditions wherein cell death occurs by apoptosis includes, but are not limited to, stroke, head trauma, Bell's palsy, spinal cord and other nerve crush injuries, Alzheimer's disease, Parkinson's disease, Pick's disease, amyotrophic lateral sclerosis, Huntington's disease, multiple sclerosis, cardiac myopathies, nephropathy, retinopathy, diabetic complications, glaucoma, as well as idiopathic neuropathies.

Pharmaceutical Compositions

The compounds of the general formula I may be formulated into pharmaceutical compositions for administration to subjects in a biologically compatible form suitable for administration in vivo. The compositions containing the compounds of the invention can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The active substance may be administered in a convenient manner such as by injection (subcutaneous, intravenous, etc.), oral administration, inhalation, transdermal application, or rectal administration.

In oral administration, the compounds may be administered as tablets, coated tablets, gelatine capsules, capsules, cachets, and solutions or suspensions to be taken orally. The compounds can also be administered parenterally or through any other suitable administrative route such as intravenous, subcutaneous, depot injections, intramuscular, intrathecal, intraventricular, intra-articular, rectal (suppository, enema), sublingual, buccal, intra-ocular, intra-vitreo, transdermal (skin patch), nasal drops (nebulizer, insufflation), liposomal delivery systems. The daily dosage could likely range from 1 to 100 mg.

Accordingly, in another aspect, the present invention provides a pharmaceutical composition comprising a compound of general formula (I) in admixture with a suitable diluent or carrier. The compound may be achiral or a substantially enantiomerically pure R- or S-enantiomer, or a pharmaceutically acceptable salt thereof, in admixture with pharmaceutically acceptable diluents or carriers. The compositions are useful in the treatment or prevention of conditions in which cell death occurs by apoptosis.

In another aspect, the present invention provides a commercial package containing as active ingredient a compound of the formula I, or a pharmaceutically acceptable salt thereof, together with instructions for its use for the treatment or prevention of a condition in which cell death occurs by apoptosis.

EXAMPLES

Example 1

In Vitro Protocol for Assessing the Antiapoptotic Capacity of Various Compounds in Cerebellar Granule Cells The following biological data demonstrate that the compounds of the invention exhibit antiapoptotic properties.

Cultures of cerebellar granule cells (CGC) can be induced into apoptosis by the addition of a high concentration of cytosine arabinoside (AraC) [27]. It has been shown that this is a p53 dependent apoptosis [28]. We have measured the antiapoptotic effect of some amino acids, amino esters, amino phosphonic acids, amino nitriles and amino tetrazoles using this system.

Cultures of CGC were obtained from 6–8 day old Wistar rat pups. Cultures were grown on glass in 35 mm petri dishes for three days and then used for experiments. Aliquots (20 ul) of drug solutions (AraC, anti-apoptotic drugs, drug vehicles) were added to the medium of the culture. 24 Hours later the cultures were fixed with FAM, and stained with bis-benzamide. Normal and apoptotic nuclei were counted to a total of 90–120 cells per culture. The optimum concentration of AraC was found to be 300 uM.

The results are summarized in Tables 1–4.

TABLE 1

Rescue by Amino Acids and Esters in the CGC Assay

| Compound | $10^{-6}$ M | $10^{-9}$ M | $10^{-12}$ M | Rescue |
|---|---|---|---|---|
| Glycines (aminoacetic acids) | | | | |
| 2-Propyl | R | X | X | yes |
| 1-Hexyl | X | R | X | yes |
| R-2-Heptyl | X | X | X | no |
| S-2-Heptyl | R | R | R | yes |
| B-Alanines (aminopropionic acids) | | | | |
| 2-Propyl | X | R | R | yes |
| 2-Propyl-N-methyl | R | R | X | yes |
| R-2-Pentyl | X | X | X | no |
| 1-Hexyl | R | R | R | yes |
| 1-Hexyl-N-methyl | R | R | X | yes |
| R-2-Heptyl | | R | R | yes |
| R-2-Heptyl-N-methyl | R | R | R | yes |
| S-2-Heptyl | | | X | no |
| B-Alaninates (esters) | | | | |
| 2-Propyl | X | X | X | no |
| 1-Hexyl | X | R | R | yes |
| R-2-Heptyl-N-methyl | R | R | R | yes |

R = rescue; X = no rescue

TABLE 2

Rescue by Amino Phosphonic Acids in the CGC Assay

| Compound | $10^{-6}$ M | $10^{-9}$ M | $10^{-12}$ M | Rescue |
|---|---|---|---|---|
| 2-Propyl | R | R | R | yes |
| R-2-Pentyl | R | X | X | yes |
| 1-Hexyl | X | X | X | no |
| R-2-Heptyl | R* | X | X | yes* |
| S-2-Heptyl | X | R | R | yes |

*The presence of 0.5% S-enantiomer (which is potent at $10^{-12}$ M) in the R-enantiomer is probably responsible for the apparent rescue by the R-enantiomer at $10^{-6}$ M.

TABLE 3

Rescue by Amino Tetrazoles in the CGC Assay

| Compound | $10^{-6}$ M | $10^{-9}$ M | $10^{-12}$ M | Rescue |
|---|---|---|---|---|
| R-2-Heptyl | R | R | R | yes |
| S-2-Heptyl | X | X | X | no |

TABLE 4

Rescue by Amino Nitriles in the CGC Assay

| Compound | $10^{-6}$ M | $10^{-9}$ M | $10^{-12}$ M | Rescue |
|---|---|---|---|---|
| Acetonitriles | | | | |
| 2-Propyl | R | R | R | yes |
| R-2-Pentyl | X | R | X | yes |
| S-2-Pentyl | X | X | X | no |
| 1-Hexyl | X | R | R | yes |
| R-2-heptyl | X | X | X | no |
| S-2-Heptyl | X | R | R | yes |
| Propionitriles | | | | |
| 2-Propyl | X | X | X | no |
| 2-Propyl-N-methyl | T | T | X | no |
| R-2-Pentyl | X | X | X | no |
| tert-Amyl | X | X | X | no |
| tert-Amyl-N-methyl | X | X | X | no |
| 3-Pentyl | R | R | X | yes |
| 1-Hexyl | X | X | X | no |
| 1-Hexyl-N-methyl | X | X | X | no |
| R-2-Heptyl | X | R | R | yes |
| R-2-Heptyl-N-methyl | X | R | X | yes |
| S-2-heptyl | X | X | X | no |

R = rescue; X = no rescue; T = toxic

Detailed Synthetic Procedures

The following non-limiting examples of synthetic procedures are provided.

Example 2

Methyl 3-(1-hexylamino)propionate hydrochloride [Methyl N-(1-hexyl)-β-alaninate]

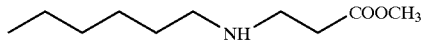

To ice-water-cooled 1-hexylamine (7.58 g, 75 mmol) was added dropwise methyl acrylate (4.3 g, 50 mmol). After completion of the addition the temperature was allowed to rise to room temperature and the reaction solution was stirred for 5 hours, then refluxed for 90 minutes. After stirring overnight at 20° C. the product, methyl 3-(1-hexylamino)propionate, was distilled (b.p.=85–88° C./2 mm; lit. b.p. 80–84° C./0.5 mm) as a clear, colorless liquid in a yield of 55%. The hydrochloride salt was prepared by the addition of methanolic HCl (15%) to an ethereal solution of the free base; m.p.=204–205° C. (lit. m.p. 190–192° C.).

Mass spectrum: m/e: 187 (M+); 116 (M—$C_5H_{11}$); 84.

Example 3

(R)-Methyl 3-(2-heptylamino)propionate hydrochloride [(R)-Methyl N-(2-heptyl)-β-alaninate]

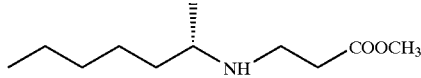

Prepared according to Example 2. The hydrochloride salt was recrystallized from methanol/ether; m.p.=89.5–90.5° C.

Mass spectrum: m/e: 201 (M+); 186 (M—$CH_3$); 130 (M—$C_5H_{11}$)

Example 4

Methyl 3-(2-propylamino)propionate hydrochloride [Methyl N-(2-propyl)-β-alaninate]

Prepared according to Example 2. The hydrochloride salt was crystallized from methanol/ether; m.p.=108–110° C. (lit. m.p. 107° C.).

Mass spectrum: m/e: 145 (M+); 130 (M—$CH_3$); 98; 72; 56.

Example 5

(R)-3-(2-Heptylamino)propionic acid hydrochloride [(R)-N-(2-heptyl)-β-alanine]

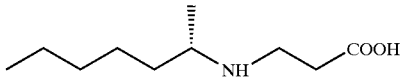

(R)-3-(2-Heptylamino)propionitrile (75 g, 44.6 mmol) (prepared according to Example 18) was refluxed with concentrated hydrochloric acid (50 mL) for 4 h. After filtration of insoluble ammonium chloride, the aqueous solution was rotary evaporated to dryness. The residue was stirred with dichloromethane (120 mL) for 2 hours and the insoluble ammonium chloride was filtered. The filtrate was concentrated, filtered again and then evaporated to give a colorless oil which crystallized on cooling. The yield of white hygroscopic product was quantitative; m.p.=57–58° C.

Mass spectrum: m/e: 187 (M+); 172 (M—$CH_3$); 116 (M—$C_5H_{11}$); 72.

1H-NMR ($D_2O$, 300 MHz): 0.72 (t, 3H); 1.18 (d, 3H); 1.1–1.3 (m, 6H); 1.42/1.60 (2m, 1H each); 2.67 (t, 2H); 3.17 (m, 3H; αCH & $CH_2COOH$).

The title compound can also be prepared by hydrochloric acid hydrolysis of the methyl ester (prepared according to Example 3).

Example 6

(S)-3-(2-Heptylamino)propionic acid hydrochloride [(S)-N-(2-heptyl)-β-alanine]

Prepared according to Example 5. The hydrochloride salt, m.p.=56–58° C., is hygroscopic.

Mass spectrum: m/e: 187 (M+); 172 (M—$CH_3$); 128 (M—$CH_2COOH$); 116 (M—$C_5H_{11}$).

1H-NMR ($D_2O$, 300 MHz): 0.75 (t, 3H); 1.18 (d, 3H); 1.1–1.3 (m, 6H); 1.45/1.60 (2m, 1H each); 2.68 (t, 2H); 3.20 (m, 3H; αCH & $CH_2COOH$).

Example 7

3(1-Hexylamino)propionic acid [N-(1-hexyl)-β-alanine]

Methyl 3-(1-hexylamino)propionate hydrochloride (see Example 2 for preparation) was hydrolyzed by refluxing in 2N HCl for 24 hours followed by evaporation to dryness; m.p.=95–97° C. (no lit. value).

Mass spectrum: m/e: 173 (M+); 102 (M—$C_5H_{11}$); 84; 72.

1H-NMR ($D_2O$, 300 MHz): 0.73 (t, 3H); 1.17 (m, 6H); 1.52 (m, 2H); 2.68 (t, 2H); 2.93 (t, 2H); 3.18 (t, 2H).

Example 8

3-(2-Propylamino)propionic acid hydrochloride [N-(2-propyl)-β-alanine]

Prepared by hydrolysis of the ester (Example 7). The product is a white powder, m.p.=154–155° C. (no lit. value).

Mass spectrum: m/e: 131 (M+); 116 (M—$CH_3$); 98; 56.

1H-NMR ($D_2O$, 300 MHz): 1.20 (d, 6H); 2.70 (t, 2H); 3.19 (t, 2H); 3.32 (m, 1H).

Example 9
Ethyl 2-(2-propylamino)acetate hydrochloride [Ethyl N-(2-propyl)glycinate]

To a solution of 2-propylamine (4.4 g, 75 mmol) in ether (100 mL) was added ethyl bromoacetate (6.26 g, 37.5 mmol). The solution was stirred at 20° C. for 3 days. The precipitated 2-propylamine hydrobromide was filtered and the filtrate rotary evaporated to give 5.4 g a clear pale yellow liquid (crude yield=99%). The hydrochloride salt was prepared and recrystallized from ethanol/ether; m.p.=120–121° C. (no lit. value).
Mass spectrum: m/e: 145 (M+); 130 (M—$CH_3$); 72 (M—$COOC_2H_5$).

Example 10
2-(2-Propylamino)acetic acid hydrochloride [N-(2-Propyl)glycine]

The sample was prepared from the nitrile (prepared according to Example 25) in 72% yield using a hydrolysis procedure similar to that described in Example 12. The hydrochloride salt was recrystallized from acetone; m.p.=180–184° C. (lit. m.p.203–204.5° C.; 182–183° C.).
Mass spectrum: (CI). 118 (M+1); 102 (M—$CH_3$); 72 (M—$CO_2H$); (EI). 117 (M+); 102 (M—$CH_3$); 72 (M—COOH).
1H-NMR ($D_2O$, 300 MHz): 1.19 (d, 6H); 3.33 (m, 1H); 3.79 (s, 2H).

Example 11
2-(1-Hexylamino)acetic acid hydrochloride [N-(1-Hexyl)glycine] 1HxActAc The sample was prepared from the nitrile (procedure analogous to that described in Example 10) in 72% yield using a hydrolysis procedure similar to that described in Example 12. The hydrochloride salt was recrystallized from acetone; m.p.=162–164° C. (lit. m.p. 215–218° C.).
Mass spectrum: m/e: 159 (M+); 114 (M—$CO_2H$); 88 (M—$C_5H_{11}$).
1H-NMR ($D_2O$, 300 MHz): 0.72 (t, 3H); 1.20 (m, 6H); 1.55 (m, 2H); 2.96 (t, 2H); 3.77 (s, 2H).

Example 12
(R)-2-(2-Heptylamino)acetic acid hydrochloride [(R)-N-(2-Heptyl)glycine]

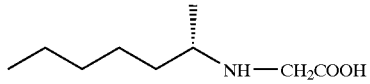

A solution of (R)-2-(2-heptylamino)acetonitrile (1.20 g, 7.79 mmol) (prepared according to Example 23) in concentrated HCl (12 mL) and water (5 mL) was heated for 48 hours at 90° C. After cooling to room temperature, the reaction mixture was concentrated to dryness, filtered, and washed with ethanol to remove $NH_4Cl$. The resulting filtrate was concentrated to give a crude product (1.40 g). A solution of the crude product (0.60 g) in concentrated HCl (20 mL) and water (10 mL) was heated for 24 hours at 90° C. After cooling to room temperature, the reaction mixture was taken to dryness and triturated in ether to give the hydrochloride salt as a crystalline solid (0.60 g, overall 37% yield); m.p.=162–164° C.

Mass spectrum: m/e: (CI). 174 (M+1); 158 (M—$CH_3$); 102 (M—$C_5H_{11}$).
1H-NMR ($D_2O$, 300 MHz): 0.74 (t, 3H); 1.18 (d, 3H); 1.1–1.3 (m, 6H); 1.45/1.60 (2m, 1H each); 3.21 (m, 1H); 3.79 (s, 2H).

Example 13
(S)-2-(2-Heptylamino)acetic acid hydrochloride [(S)-N-(2-Heptyl)glycine]

The product was prepared as described in Example 12 in 72% overall yield by hydrolysis of the nitrile hydrochloride salt; m.p.=161–163° C.
Mass spectrum: m/e: (CI). 174 (M+1); 156 (M—OH); 128 (M—$CO_2H$).
1H-NMR ($D_2O$, 300 MHz): 0.73 (t, 3H); 1.18 (d, m; 9H); 1.47, 1.60 (2m, 1H each); 3.21 (m, 1H); 3.78 (s, 2H).

Example 14
Methyl 3-(2-propylmethylamino)propionate hydrochloride [Methyl N-(2-propyl)-N-methyl-β-alaninate]

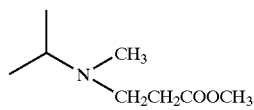

To a solution of methyl 3-(2-propylamino)propionate hydrochloride (Example 10) (0.907 g; 5 mmol) in 1N sodium dihydrogen phosphite (25 mL) was added 37% formaldehyde (2.1 mL, 23 mmol). The solution was stirred at 60° C. for 10 min, then cooled in an ice-water bath and basified with 10% sodium hydroxide (10 mL). The resulting solution was saturated with sodium chloride (9 g) and immediately extracted with ether (3×15 mL). The combined filtrates were dried over anhydrous magnesium sulfate and evaporated to dryness to give a clear colorless liquid. The hydrochloride salt, prepared by the addition of methanolic HCl to an ether solution of the free base, precipitated as a viscous oil in 83% yield.
Mass spectrum: m/e: 159 (M+); 144 (M—$CH_3$); 86 (M—$CH_2COOCH_3$).

Example 15
(R)-Methyl 3-(2-heptylmethylamino)propionate hydrochloride [(R)-Methyl N-(2-heptyl)-N-methyl-β-alaninate]

The hydrochloride salt was obtained in 93% yield as a colorless viscous liquid.
Mass spectrum: m/e: 215 (M+); 200 (M—$CH_3$); 144 (M—$C_5H_{11}$).

Example 16
(R)-3-(2-Heptylmethylamino)propionic acid hydrochloride [N-(2-Heptyl)-N-methyl-β-alanine]

The hydrochloride salt precipitated as a colorless, viscous oil.
Mass spectrum: m/e: 201 (M+); 186 (M—$CH_3$); 130 (M—$C_5H_{11}$).
1H-NMR ($D_2O$, 300 MHz): 0.72 (t, 3H); 1.18 (m, 9H); 1.47, 1.59 (2m, 1H each); 2.65 (d, 3H); 2.74 (t, 2H); 3.11 (m, 1H); 3.34 (m, 2H).

Example 17
(R)-3-(2-Heptylamino)propionitrile hydrochloride

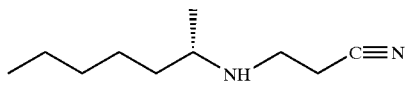

To ice-water-cooled (R)-2-heptylamine (99.4% R) (9.28 g, 80.7 mmol) was added dropwise acrylonitrile (2.85 g, 3.543 mL, 54 mmol). After completion of the addition the temperature was allowed to rise to room temperature and the reaction solution was stirred for 5 hours, then refluxed for 90 minutes. After stirring overnight at 20° C. the product, (R)-3-(2-heptylamino)propionitrile, was distilled as a clear, colorless liquid, b.p.=101–102° C./2 mm, with a yield of 85%. The hydrochloride salt was prepared by the addition of ethanolic HCl (15%) to an ethereal solution of the free base; m.p.=134–135° C.
Mass spectrum: m/e: (CI) 169 (M+H)+; 153 (M—CH$_3$); 97 (M—C$_5$H$_{11}$).
1H-NMR (D$_2$O, 300 MHz): 0.73 (t, 3H); 1.20 (d, m; 9H); 1.45, 1.61 (2m, 1H each); 2.85 (t, 2H); 3.3 (m, 3H).
Elemental Analysis: Calculated: % C=58.66; % H=10.34; % N=13.68.
Found: % C=58.73; % H=10.53; % N=13.47.

The starting material, (R)-2-heptylamine, was resolved from the racemate by repeated recrystallizations of its L-tartrate salt from methanol. Eight recrystallizations using a ratio of volume (of methanol) to weight (of tartrate salt) of 2.4 to 2.6 (increasing as optical purity increased) gave the R-enantiomer with an optical purity of 99.4% R. The optical purity was assessed by derivatization with freshly prepared chiral reagent (S)-N-trifluoroacetylpropyl chloride and then gas chromatography on a chiral column [23].

Example 18
(S)-3-(2-Heptylamino)propionitrile hydrochloride (S)-2-Heptylamine as its D-tartrate salt was prepared by recrystallization of the racemate (S-enriched, isolated and prepared from the combined filtrates of the R-enantiomer L-tartrate recrystallizations described in Example 17). The optical purity was 99.4% S. S-2HECN was prepared in 85% yield (b.p. 99–100° C./2 mm) as described for the R-enantiomer in Example 17. The hydrochloride salt was recrystallized from methanol/ether; m.p.=133–134° C.
Mass spectrum: m/e: (CI) 169 (M+H)+; 153 (M—CH$_3$); 128 (M—CH$_2$CN); 97 (M—C$_5$H$_{11}$).
1H-NMR (D$_2$O, 300 MHz): 0.72 (t, 3H); 1.20 (d, m; 9H); 1.45, 1.62 (2m, 1H each); 2.85 (t, 2H); 3.29 (m, 3H).
Elemental Analysis: Calculated: % C=58.66; % H=10.34; % N=13.68.
Found: % C=58.61; % H=10.10; % N=13.42.

Example 19
3-(2-Propylamino)propionitrile hydrochloride

The free base, b.p.=94° C./30 mm (lit. b.p. 86–87° C./17 mm), was prepared according to the procedure in Example 17 and then converted to the hydrochloride salt which was recrystallized from methanol/ether; m.p.=145.5–146° C. (no lit. value).
Mass spectrum: m/e: 140 (M+); 97 (M—CH$_3$); 72 (M—CH$_2$CN).
1H-NMR (D$_2$O, 300 MHz): 1.20 (d, 6H); 2.85 (t, 2H); 3.29 (t, 2H); 3.36 (m, 1H).

Example 20
3-(1-Hexylamino)propionitrile hydrochloride

The hydrochloride salt was recrystallized from ethanol/ether; m.p.=188–189° C. (no lit. value).
Mass spectrum: m/e: 154 (M+); 114 (M—CH$_2$CN); 83 (M—C$_5$H$_{11}$).
1H-NMR (D$_2$O, 300 MHz): 0.72 (t, 3H); 1.18 (m, 6H); 1.53 (m, 2H); 2.87 (t, 2H); 2.96 (t, 2H); 3.29 (t, 2H).

Example 21
3-(3-Pentylamino)propionitrile hydrochloride

The free base, b.p.=84–85° C./2 mm (no lit. value), was converted to the hydrochloride salt, m.p.=118.5–119.5° C. (no lit. value).
Mass spectrum: m/e: 140 (M+); 111 (M—C$_2$H$_5$); 100 (M—CH$_2$CN); 82; 70.
1H-NMR (D$_2$O, 300 MHz): 0.83 (t, 6H); 1.64 (m, 4H); 2.89 (t, 2H); 3.10 (m, 1H); 3.33 (t, 2H).

Example 22
3-(t-Amylamino)propionitrile hydrochloride

The free base, b.p.=62–63° C./2 mm (no lit. value), was converted to the hydrochloride salt, m.p.=199–200° C. (no lit. value).
Mass spectrum: m/e: 140 (M+, absent); 125 (M—CH$_3$); 111 (M—CH$_2$CH$_3$)
1H-NMR (D$_2$O, 300 MHz): 0.82 (t, 3H); 1.20 (s, 6H); 1.58 (q, 2H); 2.83 (t, 2H); 3.29 (t, 2H).

Example 23
(R)-2-(2-Heptylamino)acetonitrile hydrochloride

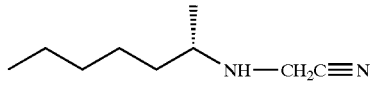

To a solution of (R)-2-heptylamine (1.90 g, 16.5 mmol) in ether (25 mL) were added anhydrous Na$_2$CO$_3$ (1.60 g, 14.9 mmol), and bromoacetonitrile (0.92 mL, 13.2 mmol). The reaction mixture was stirred at room temperature for 24 hours, and for another 14 hours at 80° C. After cooling to room temperature, the reaction mixture was filtered and the filtrate washed with HCl (3 N, 3×10 mL). The aqueous layer was basified with NaOH (6 N) and extracted with ether (3×25 mL). The resulting ethereal solution was dried over Na$_2$SO$_4$, and evaporated to dryness. The residue was fractionated by flash column chromatography (25% EtOAc/hexane, ether) to give a colorless oil (2.10 g, 82%). The hydrochloride salt was prepared by the addition of ethanolic HCl (15%) to an ethereal solution of the free base; m.p.=152–3° C.
Mass spectrum: m/e: (CI). 155 (M+1); 128 (M—CN); (EI) 139 (M—CH$_3$); 83 (M—C$_5$H$_{11}$).
1H-NMR (D$_2$O, 300 MHz): 0.75 (t, 3H); 1.20 (d, 3H); 1.15–1.35 (m, 6H); 1.47/1.62 (2m, 1H each); 3.35 (m, 1H); 4.18 (s, 2H).
Elemental Analysis: Calculated: % C=56.68; % H=10.04; % N=14.69.
Found: % C=56.81; % H=10.20; % N=14.46.

Example 24
(S)-2-(2-Heptylamino)acetonitrile hydrochloride

The sample was prepared in 96% yield using the above-described procedure (Example 23). The hydrochloride salt was prepared by the addition of ethanolic HCl (15%) to an ethereal solution of the free base and was recrystallized from ethanol/ether. The salt sublimes during melting; m.p.=140° C.

Mass spectrum: m/e: 154 (M+); 139 (M—CH$_3$).
1H-NMR (D$_2$O, 300 MHz): 0.73 (t, 3H); 1.18 (d, m; 9H); 1.43, 1.59 (2m, 1H each); 3.31 (m, 1H); 4.15 (s, 2H).
Elemental Analysis: Calculated: % C=56.68; % H=10.04; % N=14.69.
Found: % C=56.51; % H=9.71; % N=14.79.

Example 25
2-(2-Propylamino)acetonitrile hydrochloride
The hydrochloride salt was recrystallized from methanol/ether; m.p.=166–167° C. (lit. m.p. 154–156°).
Mass spectrum: m/e: 98 (M+); 83 (M—CH$_3$); 56.
1H-NMR (D$_2$O, 300 MHz): 1.19 (d, 6H); 3.45 (m, 1H); 4.17 (s, 2H).

Example 26
2-(1-Hexylamino)acetonitrile hydrochloride
The free base of the sample was prepared in 62% yield using the above-described procedure (Example 23). The hydrochloride salt was prepared by the addition of ethanolic HCl (15%) to an ethereal solution of the free base, and was recrystallized from ethanol/ether; m.p.=114–115° C. (lit. m.p. 84–86° C.).
Mass spectrum: m/e: (CI). 141 (M+1)+; 126 (M—CN).
1H-NMR (D$_2$O, 300 MHz): 0.74 (t, 3H); 1.21 (m, 6H); 1.58 (m, 2H); 3.08 (t, 2H); 4.17 (s, 2H).

Example 27
(R)-3-(2-Heptylmethylamino)propionitrile hydrochloride

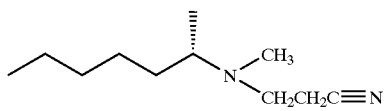

(R)-3-(2-Heptylamino)propionitrile (Example 17) (0.85 g, 5.0 mmol) was dissolved in 1N sodium dihydrogen phosphite (NaH$_2$PO$_3$) (25 mL) and 37% formaldehyde (2.1 mL, 23 mmol) was added. Sufficient dioxan was added to give a clear solution (10 mL). The solution was stirred at 60° C. for 15 min during which time it became cloudy. To the cooled solution was then added 20% sodium hydroxide (20 mL) and sodium chloride (9 g). The basic solution was extracted with ether (3×15 mL). The combined extracts were dried over anhydrous magnesium sulfate and then evaporated to give a clear, colorless liquid in quantitative yield. The hydrochloride salt was prepared by adding methanolic HCl to an ether solution of the free base; m.p.=98–98.5° C. Overall yield was 85%.
Mass spectrum: m/e: 182 (M+); 167 (M—CH$_3$); 142 (M—CH$_2$CN); 111 (M—C$_5$H$_{11}$).
1H-NMR (D$_2$O, 300 MHz): 0.77 (t, 3H); 1.20 (d, 3H); 1.15–1.35 (m, 6H); 1.50/1.62 (2m, 1H each); 2.73 (s, 3H); 2.95 (t, 2H); 3.40 (m, 3H; aCH & CH$_2$CN).
Elemental Analysis: Calculated: % C=60.39; % H=10.60; % N=12.80.
Found: % C=59.55; % H=10.29; % N=13.67.

Example 28
3-(2-Propylmethylamino)propionitrile hydrochloride
The hydrochloride salt was obtained in 90% yield; m.p.=121–121.5° C. (no lit. value) (see Example 27).
Mass spectrum: m/e: 126 (M+); 111 (M—CH$_3$); 86 (M—CH$_2$CN).
1H-NMR (D$_2$O, 300 MHz): 1.23 (d, 6H); 2.73 (s, 3H); 2.97 (t, 2H); 3.52 (br s, 2H); 3.60 (m, 1H).

Example 29
3-(t-Amylmethylamino)propionitrile hydrochloride
The hydrochloride salt was obtained in 87% yield; m.p.=137–138° C. (no lit. value) (see Example 27).
Mass spectrum: m/e: 154 (M+); 139 (M—CH$_3$); 125 (M—C$_2$H$_5$); 72.
1H-NMR (D$_2$O, 300 MHz): 0.87 (t, 3H); 1.25 (6H); 1.67 (q, 2H); 2.10 (s, 2H); 2.73 (s, 3H); 2.94 (broad t, 2H).
Elemental Analysis: Calculated: % C=56.68; % H=10.04; % N=14.69.
Found: % C=56.62; % H=10.12; % N=14.62.

Example 30
3-(1-Hexylmethylamino)propionitrile hydrochloride
The hygroscopic hydrochloride salt was obtained in 75% yield; m.p.=77–78.5° C. (no lit. value) (see Example 27).
Mass spectrum: m/e: 168 (M+); 128 (M—CH$_2$CN); 97 (M—C$_5$H$_{11}$).
1H-NMR (D$_2$O, 300 MHz): 0.72 (t, 3H); 1.20 (m, 6H); 1.60 (m, 2H); 2.79 (s, 3H); 2.95 (t, 2H); 3.09 (t, 2H); 3.42 (t, 2H).

Example 31
Diethyl 2-(2-propylamino)ethanephosphonate hydrochloride

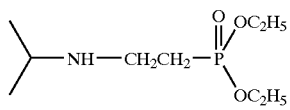

To ice-cooled 2-propylamine (0.53 mL, 6.2 mmol) was added dropwise diethyl vinylphosphonate (0.4 mL, 3.1 mmol) under N$_2$. The reaction mixture was stirred for 2 hours at 0° C., for 14 hours at room temperature, and for 10 hours at 100° C. After cooling to room temperature, the reaction mixture was concentrated to give a colorless oil (0.89 g). To a solution of the crude product (0.89 g) in ether (40 mL) was added ethanolic HCl (15%), and then stirred for 2 hours at room temperature. The resulting crystallized hydrochloride salt was filtered, washed with ether to give a white solid (0.76 g, overall 95%); m.p.=96–97° C. (no lit. value).
Mass spectrum: m/e: 208 (M—CH$_3$)+; 180 (M—C$_3$H$_7$)+.

Example 32
2-(2-Propylamino)ethanephosphonic acid hydrochloride
The hydrochloride salt of the product (starting from the diester, Example 31) was prepared in 32% overall yield using the procedure described in Example 37; m.p.=164–166° C. (no lit. value).
Mass spectrum: m/e: (CI). 168 (M+1)+.
1H-NMR (D$_2$O, 300 MHz): 1.16 (d, 6H); 1.84 (m, 2H); 3.08 (q, 2H); 3.27 (m, 1H).

Example 33
Diethyl 2-(1-hexylamino)ethanephosphonate hydrochloride
The crude product was prepared in 100% yield using the above-described procedure. The hydrochloride salt of the product was prepared by the addition of ethanolic HCl (15%) to an ethereal solution of the product; the salt is a viscous oil.
Mass spectrum: m/e: 265 (M)+, 194 (M—C$_5$H$_{11}$)+.

Example 34
2-(1-Hexylamino)ethanephosphonic acid hydrochloride
The hydrochloride salt was prepared by hydrolysis of the diethyl ester using the method described in Example 37; m.p.=145–150° C. (no lit. value).

Mass spectrum: m/e: too involatile

1H-NMR (D$_2$O, 300 MHz): 0.70 (t, 3H); 1.15 (m, 6H); 1.50 (m, 2H); 1.90 (m, 2H); 2.88 (t, 2H); 3.08 (q, 2H).

Elemental Analysis: Calculated: % C=39.11; % H=8.62; % N=5.70.

Found: % C=39.34; % H=8.53; % N=5.89.

Example 35

(R)-Diethyl 2-(2-heptylamino)ethanephosphonate hydrochloride

The free base was prepared in 93% yield using the above-described procedure. The hydrochloride salt was prepared by the addition of ethanolic HCl (15%) to an ethereal solution of the product; the salt is a viscous oil.

Mass spectrum: m/e: (CI). 280 (M+1)+; 264 (M—CH$_3$)+; 208 (M—C$_5$H$_{11}$)+.

Example 36

(S)-Diethyl 2-(2-heptylamino)ethanephosphonate hydrochloride

The free base was prepared in 91% yield using the above-described procedure. The hydrochloride salt was prepared by the addition of ethanolic HCl (15%) to an ethereal solution of the product; the salt is a viscous oil.

Mass spectrum: m/e: (CI). 280 (M+1)+; 208 (M—C$_5$H$_{11}$)+.

Example 37

(R)-2-(2-Heptylamino)ethanephosphonic acid hydrochloride

A solution of (R)-diethyl 2-(2-heptylamino) ethanephosphonate hydrochloride (0.19 g, 0.68 mmol) in concentrated HCl (7 mL) was heated at 90° C. for 48 hours. The reaction mixture was then evaporated to dryness and the residue triturated with acetone. The white solid was filtered and air-dried giving an 86% overall yield; m.p.=106–112° C. (no lit. value).

Mass spectrum: m/e: too involatile

1H-NMR (D$_2$O, 300 MHz): 0.73 (t, 3H); 1.25–1.10 (m, 12H); 1.43 (m, 1H); 1.58 (m, 1H); 1.89–1.78 (m, 2H); 3.22–3.05 (m, 3H).

Elemental Analysis: Calculated: % C=41.62; % H=8.93; % N=5.39.

Found: % C=41.68; % H=9.10; % N=5.23.

Example 38

(S)-2-(2-Heptylamino)ethanephosphonic acid hydrochloride

The hydrochloride salt was prepared in 71% overall yield using the above described procedure; m.p.=106–113° C. (no lit. value).

Mass spectrum: m/e: too involatile

1H-NMR (D$_2$O, 300 MHz): 0.73 (t, 3H); 1.25–1.10 (m, 12H); 1.44 (m, 1H); 1.59 (m, 1H); 1.89–1.78 (m, 2H); 3.22–3.05 (m, 3H).

Elemental Analysis: Calculated: % C=41.62; % H=8.93; % N=5.39.

Found: % C=41.43; % H=9.09; % N=5.33.

Example 39

(R)-2-(2-Heptylamino)ethane-5-tetrazole hydrochloride

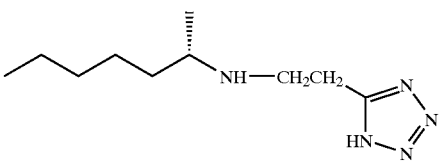

The compound as its hydrochloride salt was prepared in 28% overall yield using the procedure described below in Example 40; the salt is a viscous oil.

Mass spectrum: m/e: (CI). 140 (M—C$_5$H$_{11}$)+; 128 (M—C$_2$H$_3$N$_4$)+.

1H-NMR (D$_2$O, 300 MHz): 0.71 (t, 3H); 1.18 (m, 9H); 1.44, 1.60 (2m, 1H each); 3.30 (t+m; 3H); 3.45 (m, 2H).

Example 40

(S)-2-(2-Heptylamino)ethane-5-tetrazole hydrochloride

To an ice-cooled suspension of NaN$_3$ (2.60 g, 40 mmol) in dry THF (20 mL) was added AlCl$_3$ (1.36 g, 10 mmol) in portions under N$_2$, and stirred for 30 minutes. To the resulting suspension was added a solution of (S)-3-(2-heptylamino)propionitrile (1.68 g, 10 mmol) in THF (10 mL), and stirred for 2 hours at 0° C., then gently refluxed for 24 hours. After cooling to room temperature, the reaction mixture was quenched by the careful addition of HCl (3 N, 15 mL), water (5 mL), and the two layers were separated. The lower aqueous layer was extracted with ethyl acetate (3×15 mL). The upper (organic) layer and the organic extracts were combined and dried over Na$_2$SO$_4$, then taken to dryness to give crude product (oil, 1.36 g). The oil was diluted with ether (30 mL) and ethanol (5, mL), stirred for two hours, and filtered to give the hydrochloride salt (0.21 g, 9% overall yield); m.p.=112–113° C. (no lit. value).

Mass spectrum: m/e: (CI). 140 (M—C$_5$H$_{11}$)+; 128 (M—C$_2$H$_3$N$_4$)+.

1H-NMR (D$_2$O, 300 MHz): 0.72 (t, 3H); 1.20 (d, 3H); 1.15–1.35 (m, 6H); 1.45/1.62 (2m, 1H each); 3.30 (t+m; 3H); 3.43 (m, 2H).

Elemental analysis: Calculated: % C=48.47; % H=8.95; % N=28.27.

Found: % C=48.24; % H=8.85; % N =28.40.

FULL CITATIONS FOR REFERENCES REFERRED TO IN THE SPECIFICATION

1. Ansari, K. S., et al., Rescue of axotomized immature rat facial motoneurons by R(-)-deprenyl: stereospecificity and independence from monoamine oxidase inhibition. Journal of Neuroscience, 1993. 13: p. 4042–4053.

2. Davis, B. A., et al. Neurorescue by the optically acive enantiomers of some aliphatic N-methylpropargylamines. Abstract, American Society for Neurochemistry. 1995. Santa Monica, Calif.

3. Oh, C., et al., (-)-Deprenyl alters the survival of adult murine facial motoneurons after axotomy: Increases in vulnerable C57BL strain but decreases in motor neuron degeneration mutants. J. Neurosci. Res., 1994. 38: p. 64–74.

4. Paterson, I. A., B. A. Davis, and A. A. Boulton, Aliphatic propargylamines prevent hippocampal neuronal death induced by hypoxia-ischemia. J. Neurochem., 1997. 69 (Supp): p. S137.

5. Paterson, I. A., et al., (-)-Deprenyl reduces delayed neuronal death of hippocampal pyramidal cells. Neurosci. Biobehav. Rev., 1997. 21: p. 181–186.

6. Paterson, I. A., et al., R-Deprenyl and R-2-heptyl-N-methylpropargylamine prevent apoptosis in cerebellar granule neurons induced by cytosine arabinoside but not low extracellular potassium. J. Neurochem., 1998. 98: p. 515–523.

7. Paterson, I. A., et al., The anti-apoptotic effects of 2HMP is due to a desmethyl metabolite. Society for Neuroscience Abstracts, 1997. 23 (part 2): p. 2254 (#880.6).

8. Paterson, I. A., et al., Aliphatic propargylamines as cellular rescue agents. United States Patent, filed July 14, 1997.

9. Tatton, W. G. and C. E. Greenwood, Rescue of dying neurons: a new action for deprenyl in MPTP Parkinsonism. J. Neurosci. Res., 1991. 30: p. 666–672.

10. Tatton, W. G., et al., (-)-Deprenyl reduces PC12 cell apoptosis by inducing new protein synthesis. J. Neurochem., 1994. 63: p. 1572–1575.

11. Salo, P. T. and W. G. Tatton, Deprenyl reduces the death of motoneurons caused by axotomy. J. Neurosci. Res., 1992. 31: p. 394–400.

12. Wu, R.-M., D. L. Murphy, and C. C. Chiueh, Neuronal protective and rescue effects of deprenyl against MPP+ dopaminergic toxicity. J. Neural Transm. [Gen Sect], 1995. 100: p. 53–61.

13. Yoles, E. and M. Schwartz, N-Propargyl-1 (R)-aminoindan (TVP-1012), a putative neuroprotective agent, enhance in vitro neuronal survival after glutamate toxicity. Abstract, American Society for Neuroscience. 1995. San Diego, Calif.

14. Zhang, X., et al., Immunohistochemical evidence of neuroprotection by R-(-)-deprenyl and N-(2-hexyl)-N-methylpropargylamine on DSP-4-induced degeneration of rat brain noradrenergic axons and terminals. Journal of Neuroscience Research, 1996. 43: p. 482–489.

15. Yu, P. H., Davis, B. A., Boulton, A. A., Aliphatic propargylamines as specific MAO-B inhibitors and as neuroprotective agents. U.S. Pat. No. 5,508,311 (1992).

16. Durden, D. A., et al., Aliphatic propargylamines as cellular rescue agents. U.S. Pat. No. 5,840,979 (1997).

17. Grace, J. M., M. T. Kinter, and T. L. Macdonald, Atypical metabolism of deprenyl and its enantiomer, (S)-(+)-N,alpha-dimethyl-N-propynylphenylethylamine, by cytochrome P450 2D6. Chem. Res. Toxicol., 1994. 7: p. 286–290.

18. Komives, E. A. and P. R. Ortiz de Montellano, Mechanism of oxidation of π bonds by cytochrome P-450. J. Biol. Chem., 1987. 262: p. 9793–9802.

19. Roberts, E. S., et al., Mechanism-based inactivation of cytochrome 450 2B1 by 9-ethynylphenanthrene. Arch. Biochem. Biophys., 1995. 323: p. 295–302.

20. Valoti, M., et al., Interactions between substituted tryptamine analogues, MAO inhibitors and cytochrome P-450. J. Neural Transm. [Suppl], 1994. 41: p. 291–293.

21. Tarbell, D. S., et al., The synthesis of some 7-chloro-4-(3-alkylaminopropylamino)quinolines. J. Am. Chem. Soc., 1946. 68: p. 1217–1219.

22. Mazur, R. H., Absolute configuration of 1-methylalkylamines. J. Organic Chemistry, 1970. 35: p. 2050–2051.

23. Durden, D. A., B. A. Davis, and A. A. Boulton, Enantioselective gas chromatographic assay of 2-alkylamines using N-(trifluoroacetyl)propyl derivatives and a chiral capillary column. Journal of Chromatography B, 1997. 689: p. 165–173.

24. Robinson, J. B. and J. Thomas, The preparation of N-t-butyl-4-piperidone. J. Chem. Soc., 1965: p. 2270–2271.

25. Arnold, C. and D. N. Thatcher, Preparation and reactions of 5-vinyltetrazole. J. Org. Chem., 1969. 34: p. 1141–1142.

26. Loibner, H., A. Pruckner, and A. Stutz, Reductive methylation of amines. Tetrahedron Lett., 1984. 25: p. 2535–2536.

27. Dessi, F., et al., Cytosine arabinoside induces apoptosis in cerebellar neurons in culture. J. Neurochem., 1995. 64: p. 1980–1987.

28. Enokido, Y., et al., P53 involves cytosine arabinoside induced apoptosis in cultured cerebellar granule neurons. Neurosci. Lett., 1996. 203: p. 1–4.

We claim:

1. A compound of the Formula I

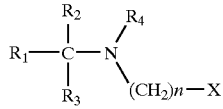

Formula I wherein:
R$_1$ is $(CH_2)_mCH_3$ where m is 0 or an integer in the range from 1 to 16, or an alkenyl, alkynyl, alkoxy, alkylthio, or alkyl sulfinyl group having from 2 to 17 carbon atoms, wherein R$_1$ may be optionally substituted with one or more substituents selected from hydroxy, aldehyde, oxo, lower acyloxy, halogen, thio, sulfoxide and sulfone, R$_2$ is H, CH$_3$ or CH$_2$CH$_3$, R$_3$ is H or CH$_3$, R$_4$ is H or CH$_3$, n is an integer in the range from 1 to 3, X is carboxyl (COOH), and R$_1$, R$_2$ and R$_3$ are each different so that the carbon atom to which they are attached is chiral and the compound of Formula I is a substantially pure enantiomer in the R or S configuration or a pharmaceutically acceptable salt thereof.

2. A compound of the Formula I according to claim 1 wherein:
R$_1$ is $(CH_2)_mCH_3$ where m is 0 or an integer in the range from 1 to 16, R$_2$ is CH$_3$, R$_3$ is H, R$_4$ is H or CH$_3$, n is an integer in the range from 1 to 3, and X is carboxyl (COOH), or a pharmaceutically acceptable salt thereof.

3. A compound of the Formula I according to claim 1 wherein:
R$_1$ is $(CH_2)_mCH_3$ where m is 0 or an integer in the range from 1 to 16, R$_2$ is CH$_3$, R$_3$ is H, R$_4$ is H or CH$_3$, n is an integer in the range from 1 to 3, and X is carboxyl (COOH), as a substantially pure enantiomer in the R-configuration, or a pharmaceutically acceptable salt thereof.

4. A compound of the formula I according to claim 1 wherein:

$R_1$ is $(CH_2)_mCH_3$ where m is 0 or an integer in the range from 1 to 16, $R_2$ is $CH_3$, $R_3$ is H, $R_4$ is H or $CH_3$, n is an integer in the range from 1 to 3, and X is carboxyl (COOH), as a substantially pure enantiomer in the S-configuration, or a pharmaceutically acceptable salt thereof.

5. A compound according to claim 3, wherein said compound of formula I is selected from the group consisting of:

(R)-3-(2-Heptylamino)propionic acid; and (R)-3-[N-(2-Heptyl)-N-methylamino]propionic acid.

6. A compound according to claim 4, wherein said compound of formula I is selected from the group consisting of:

(S)-2-(2-Heptylamino)acetic acid; and (S)-2-[N-(2-Heptyl)-N-methylamino]acetic acid.

7. A compound selected from the group consisting of:

2-(1-Hexylmethylamino)acetic acid; and

3-[N-(2-Propyl)-N-methylamino]propionic acid.

8. A compound according to claim 1 in the form of a hydrochloride salt.

9. A compound according to claim 1 wherein m is an integer from 1 to 12.

10. A compound according to claim 1 wherein m is an integer from 1 to 9.

11. A pharmaceutical composition comprising a compound having the formula I as claimed in claim 1 in admixture with a suitable diluent or carrier.

12. A composition according to claim 11, wherein:

$R_1$ is $(CH_2)_mCH_3$ where m is 0 or an integer in the range from 1 to 16, $R_2$ is $CH_3$, $R_3$ is H, $R_4$ is H or $CH_3$, n is an integer in the range from 1 to 3, and X is carboxyl (COOH).

13. A composition according to claim 11, wherein said compound of formula I is selected from the group consisting of:

(R)-3-(2-Heptylamino)propionic acid; and (R)-3-[N-(2-Heptyl)-N-methylamino]propionic acid.

14. A composition according to claim 11, wherein said compound of formula I is selected from the group consisting of:

(S)-2-(2-Heptylamino)acetic acid; and (S)-2-[N-(2-Heptyl)-N-methylamino]acetic acid.

15. A pharmaceutical composition comprising a compound selected from the group consisting of:

2-[N-(1-Hexyl)-N-methylamino]acetic acid; and

3-[N-(2-Propyl)-N-methylamino]propionic acid;

in admixture with a suitable diluent or carrier.

16. A composition according to claim 11, wherein the compound of formula I is in the form of a hydrochloride salt.

17. A method for the treatment of a disease in which cell death occurs by apoptosis comprising administering an effective amount of a compound of formula I to an animal in need thereof, wherein said compound of formula I is:

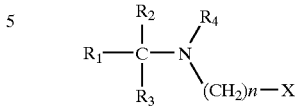

Formula I wherein:

$R_1$ is $(CH_2)_mCH_3$ where m is 0 or an integer in the range from 1 to 16, or an alkenyl, alkynyl, alkoxy, alkylthio, or alkyl sulfinyl group having from 2 to 17 carbon atoms, wherein $R_1$ may be optionally substituted with one or more substituents selected from hydroxy, aldehyde, oxo, lower acyloxy, halogen, thio, sulfoxide and sulfone, $R_2$ is H, $CH_3$ or $CH_2CH_3$, $R_3$ is H or $CH_3$, $R_4$ is H or $CH_3$, n is an integer in the range from 1 to 3, and X is carboxyl (COOH), or a pharmaceutically acceptable salt thereof, and wherein the disease is selected from the group consisting of stroke, head trauma, Bell's palsy, spinal cord injury, Alzheimer's disease, Parkinson's disease, Pick's disease, amyotrophic lateral sclerosis, Huntington's disease, multiple sclerosis, cardiac myopathies, nephropathy, retinopathy, diabetic complications, glaucoma and idiopathic neuropathies.

18. A method according to claim 17, for the treatment of a human.

19. A method according to claim 17, wherein $R_1$ is $(CH_2)_mCH_3$ where m is 0 or an integer in the range from 1 to 16, $R_2$ is $CH_3$, $R_3$ is H, $R_4$ is H or $CH_3$, n is an integer in the range from 1 to 3, and X is carboxyl (COOH), or a pharmaceutically acceptable salt thereof.

20. A method according to claim 17 wherein said compound of Formula I is selected from the group consisting of:

2-(2-Propylamino)acetic acid;

2-(1-Hexylamino)acetic acid;

(S)-2-(2-Heptylamino)acetic acid;

3-(2-Propylamino)propionic acid;

3-(1-Hexylamino)propionic acid;

(R)-3-(2-Heptylamino)propionic acid;

2-[N-Methyl-N-(2-propyl)amino]acetic acid;

2-[N-(1-Hexyl)-N-methylamino]acetic acid;

(S)-2-[N-(2-Heptyl)-N-methylamino]acetic acid;

3-[N-(2-Propyl)-N-methylamino]propionic acid;

3-[N-(1-Hexyl)-N-methylamino]propionic acid; and (R)-3-[N-(2-Heptyl)-N-methylamino]propionic acid.

* * * * *